United States Patent [19]

Drizen

[11] Patent Number: 5,077,296

[45] Date of Patent: Dec. 31, 1991

[54] METHOD FOR TREATING EQUINE NAVICULAR DISEASE WITH PENTOXIFYLLINE, AND COMPOSITION CONTAINING PENTOXIFYLLINE FOR ADMINISTRATING TO HORSES

[75] Inventor: Alan Drizen, Downsview, Canada

[73] Assignee: Hyal Pharmaceutical Corporation, Mississauga, Canada

[21] Appl. No.: 128,175

[22] Filed: Dec. 3, 1987

[51] Int. Cl.$^5$ .............................................. A01N 43/90
[52] U.S. Cl. ..................................... 514/261; 514/262
[58] Field of Search ............... 514/256, 261, 262, 657; 424/422

[56] References Cited

U.S. PATENT DOCUMENTS

| | | |
|---|---|---|
| 3,928,609 | 12/1975 | Behrakis . |
| 4,383,997 | 5/1983 | Boucher ............................. 424/253 |
| 4,460,772 | 7/1984 | Benovic et al. . |
| 4,500,530 | 2/1985 | Boucher . |
| 4,511,557 | 4/1985 | Gauri . |
| 4,975,432 | 12/1990 | Weithmann et al. ............... 514/261 |

Primary Examiner—Josephine Barr
Attorney, Agent, or Firm—Roper & Quigg

[57] ABSTRACT

A method of treating a horse suffering from navicular disease which involves administering an amount of a composition including pentoxifylline in a daily dose for a sufficient period of time effective to alleviate lameness in horses resulting from navicular disease. A pharmaceutical composition including an effective amount of pentoxifylline and a pharmaceutically acceptable carrier for alleviating lameness resulting from navicular disease.

16 Claims, No Drawings

METHOD FOR TREATING EQUINE NAVICULAR DISEASE WITH PENTOXIFYLLINE, AND COMPOSITION CONTAINING PENTOXIFYLLINE FOR ADMINISTRATING TO HORSES

BACKGROUND OF THE INVENTION

1. Field of the Invention

The present invention relates to oral veterinary pharmaceuticals containing pentoxifylline. More particularly, the present invention is directed to treating equine navicular disease with Pentoxifylline.

2. Discussion of Background and Material Information

Navicular disease has been recognized clinically for several hundred years and attempts to describe the pathology of this condition are on record for over 200 years. Traditionally navicular disease has been regarded as a degenerative (arthrotic) or inflammatory (arthritic, bursitic) process. Nevertheless, a vascular etiology was proposed as early as 1885 by Wally, and angiography was first performed in 1938 by Jones in an attempt to illustrate thrombosis of the digital arteries. More recently, Colles has proposed that the pain of navicular disease is due to ischemic bone necrosis caused by thrombosis of the distal nutrient arteries of the navicular bone. Thrombosis was demonstrated in angiographic studies and on histopathology, as a significant finding in horses with navicular disease. Independent studies have supported a vascular etiology of navicular disease.

Pentoxifylline ((1-(5-oxohexyl)-3, 7-dimethylxanthine) is a methylxanthine derivative, for example disclosed in U.S. Pat. No. 3,422,107, MOHLER et al., which has emerged at the forefront in the treatment of chronic occlusive arterial disease (COAD) in man. The most common symptom of COAD is intermittent claudication. Decreased red blood cell flexibility, arterial occlusion and artherosclerosis are the cardinal pathological features of intermittent claudication.

Pentoxifylline is classified as a haemorheological agent. It improves perfusion in ischemic tissues by at least three distinct mechanisms. First, pentoxifylline enhances red cell deformability and decreases red cell rigidity resulting in reduced viscosity of the blood. This allows the red cells to pass through narrow capillary networks. Secondly, pentoxifylline inhibits platelet aggregation. Thirdly, pentoxifylline promotes fibrinolysis. In combination, these actions serve to increase the blood flow through diseased vessels and into compromised tissues.

The effect of pentoxifylline in increasing red blood cell membrane flexibility is produced through inhibition of phosphodiesterase, which in turn causes increased intracellular cyclic-AMP and ATP levels. Pentoxifylline has a direct action on platelets to decrease aggregability and also causes release of prostacyclin ($P_gI_2$) from endothelial cells. Prostacyclin is the most potent inhibitor of platelet aggregation. The fibrinolytic action of pentoxifylline is mediated through interaction with $P_gE_1$.

U.S. Pat. Nos. 4,383,997 and 4,500,530, BOUCHER, are directed to a method of treating horses to inhibit or reduce increases in crenated red blood cells during exercise by administering to the animal a compound which inhibits influx of extracellular $Ca++$ into red blood cells, or enhances ATP content of ATP-depleted red blood cells. Examples of compounds disclosed which increase intracellular ATP include Pentoxifylline.

U.S. Pat. No. 4,511,557, GAURI is directed to a pharmaceutical compositions based on vasoactive compounds in combination with certain biological active ingredients which are capable of promoting oxygen supply which is preferably a dialysate concentrate obtained from the proteinized calf blood. Pentoxifylline is disclosed as an example of the vasoactive compound suitable for purposes of use in formulating this composition.

U.S. Pat. No. 3,928,609, BEHRAKIS relates to a vehicle for pharmaceuticals which improves absorption of the active agent in the alimentary tract. It is disclosed that compositions which include these type of compounds, such as theophylline, have been used for the treatment in the veterinary field as an asthma remedy and heart stimulant for animals.

U.S. Pat. No. 4,460,772, BENOVIC et al., relates to theophylline derivatives pertaining to immunoassays for determining theophylline in liquid media such as biological fluids.

SUMMARY OF THE INVENTION

The present invention is generally directed to the treatment of equine navicular disease with pentoxifylline.

In accordance with the present invention, a method of treating a horse suffering from navicular disease is provided which involves administering to the horse an amount of a composition including pentoxifylline in a dose effective to alleviate lameness resulting from navicular disease, preferably wherein the dose is a daily dose of between 6 gm–30 gm, with a daily dose of 6 gm being preferred. The daily dose is preferably administered tid for a period of between 4–6 weeks. The pharmaceutical composition for treating horses suffering from lameness resulting from navicular disease is preferably a mixture of pentoxifylline and a pharmaceutical acceptable carrier, such as starch or sugar, and preferably a sugar, which are present in a ratio within the range of about 1:1 to 1:20, and more preferably a ratio of about 1:13, wherein the amount of pentoxifylline is 2 gm in a dose formulated to be administered tid.

The present invention is also directed to a pharmaceutical composition which is preferably formulated into pills, such as tablets, capsules, caplets and the like, for administrating to horses for the treatment of navicular disease which includes an amount of pentoxifylline in a dose effective to alleviate lameness resulting from navicular disease, and a pharmaceutically acceptable carrier, preferably wherein the amount of pentoxifylline in the dosage formulation is within the range of 2 gm–30 gm, and the pharmaceutically acceptable carrier is a powder or particulate material, preferably selected from the group consisting of sugar and starch, with sugar being more preferred, and wherein the pentoxifylline and the sugar are present in a ratio of about 1:1 to 1:20 and preferably about 1:13. The composition preferably includes on a total weight basis about 7% pentoxifylline and about 92% sugar which is preferably at least one member selected from the group consisting of confectioners sugar, corn sugar and mixtures of confectioners sugar and corn sugar, preferably including about 8.5% confectioners sugar and 84% corn sugar, in addition to colloidal silicon dioxide preferably present at about 0.25% as well as artificial colors, preservatives, humectants, antimicrobial agents and the like with about 0.16% artificial color, such as Tartrazine Lake (34% Yellow #5) being preferred.

The most preferred composition for purposes of the present invention on a total weight basis consists essentially of about 7.2% pentoxifylline, about 8.5% confectioners sugar, about 83.895% corn sugar (Cerelose$_{tm}$), about 0.247% colloidal silicon dioxide (Sipernat 22S $_{tm}$) and about 0.158% Tartrazine Lake (34% Yellow #5).

The pharmaceutical composition for administering to horses may be formulated into a pill, such as a tablet, caplet or contained within a capsule.

DETAILED DESCRIPTION

Prior to discussing the details of the present invention, the following discussion is presented by way of giving background to the specific ailment, i.e. equine navicular disease, for which the present invention has been discovered to have specific utility.

The navicular bone, or distal sesamoid bone, is a small shuttle shaped bone that lies caudal to the articulation between the second and third phalanges. The navicular bone has an articular surface which acts to decrease the amount of concussion borne by the distal interphalangeal joint (coffin joint) by increasing the surface area of this joint. The navicular bone also has a flexor surface which provides a smooth gliding surface for the deep digital flexor tendon as it passes towards its insertion on the third phalanx. The proximal and distal borders of the navicular bone are the areas which receive the vascular supply to the bone, in the proximal and distal navicular arteries. These arteries branch out to form anastomotic networks. The medial and lateral extremities of the navicular bone serve as insertions for the proximal suspensory ligament which suspends the bone. Ventrally, support for the navicular bone is provided by the deep digital flexor tendon and the digital cushion. The navicular bursa is an important structure and extends along the flexor surface of the bone between the deep digital flexor tendon and its insertion. Navicular disease initially involves the flexor surface of the bone, adjacent to the deep digital flexor tendon, and the bursa. The articular surface is affected in advanced cases only.

Clinically, navicular disease presents as intermittent forelimb lameness which is exacerbated by hard work and which shows spontaneous remission following rest in its early stages. Navicular disease lameness is characterized by a shortened anterior phase of the stride, and a stumbling gait in which the toe makes contact first. Lameness is accentuated when the horse is circled to the affected side. The disease is usually bilateral although lameness predominates in one side or the other. Frequently following local anesthesia of the posterior digital nerves of the lame limb, a shifting lameness will be evident in the opposite forelimb. The disease has an insidious onset and a progressive course in spite of medical and/or surgical intervention. Horses eventually become unridable and are often euthanized at the advanced stage of the disease.

Navicular disease has a high morbidity in performance and pleasure horses. It has been estimated as the cause of one third of all the cases of chronic equine forelimb lameness. The 5-15 year old age group is primarily affected. Males or geldings are at a higher risk than females, and among the breeds, Quarterhorses are most commonly afflicted. An upright conformation of the pasterns, and small flat feet predispose horses to development of the disease. In addition, heavy work on hard surfaces and poor shoeing are also contributing factors.

To illustrate the advantages of pentoxifylline over existing navicular disease treatments, the following conventional treatments will be discussed herein.

1. Posterior digital neurectomy: A surgical procedure frequently performed which involves removing a segment of the nerves that supply the posterior third of the equine foot. Frequent side effects are painful neuroma formation, inability to sever collateral branches which results in failure of the procedure to resolve the pain and lameness, risk of serious injury to horse and rider because the horse loses "awareness" of his foot, and progressive pathological deterioration of the navicular bone.
2. Long term non-steroidal, anti-inflammatory treatment, e.g. phenylbutazone: The side effects include the risk of gastric and cecal ulcers and kidney damage with long term use. It is also difficult to feed regularly because of objectionable taste. The pathological deterioration of the navicular bone is progressive.
3. Intrabursal corticosteroid injections: It has been observed that less than 5% efficacy results.
4. Warfarin (Coumarin, a blood thinner): Requires vigilant monitoring of one stage prothrombin time throughout the treatment period and individual dose titration. A major disadvantage is that accidental lacerations or injuries, e.g. in pasture, can be fatal due to hemmorrhage.
5. Isoxsuorine (generic): Approximately 50% efficacy and unpredictable results. Questionable medical rationale for the use of peripheral vasodilators in occlusive vascular disease.
6. Corrective shoeing: A critical procedure, which must be undertaken with other forms of concurrent therapy. Corrective shoeing alone, does not resolve lameness in moderate to advanced cases.

An advantage of pentoxifylline over such conventional treatments is that pentoxifylline can arrest the progression of the disease by counteracting the pathogenetic mechanism of tissue hypoxia. Thus pentoxifylline constitutes a significant improvement over treatments that offer symptomatic relief only. Although not wishing to be bound by any particular theory, it is also believed that early cases of navicular disease may be arrested and/or cured by reversal of the ischemia. It is also believed that pentoxifylline may have application in laminitis, a life-threatening condition in which acute systemic toxicity results in ischemia of the sensitive laminae in the foot with eventual separation of the hoof wall from its supporting structures.

In general, veterinary drug preparations must possess special features to compensate for the fact that animals cannot self-administer prescribed medications. Hence, success of veterinary therapeutics is contingent upon the availability of an appropriate dosage form. When the treatment regime calls for serial daily medication, the oral route of administration is preferred, to eliminate the need for veterinary assistance and thus reduce the cost of treatment to the owner of the animal. For convenient medication that can be handled by lay attendants, the ideal oral medication is designed for mixing in the grain ration of the feed. Therefore, oral veterinary preparations must be chemically stable in the feed. Since horses are exceptionally selective in prehension and appetite, palatability of the formulation is a critical requirement in the equine species. Thus the development of successful Veterinary drugs entails the recognition of unique circumstances that are not encountered in human medicine.

The chemical behavior and pharmacokinetic properties of a drug substance largely dictate the formulation strategy. But with respect to veterinary pharmaceuticals, the target species must be considered in conjunction with the characteristics of the drug in question.

The present invention is based on the development of pentoxifylline for veterinary use as a formulation of an appropriate dosage form which has been discovered to be particularly effective in treating horses suffering from the equine navicular disease.

In accordance with the present invention, effective amounts of compositions including pentoxifylline may be administered internally to horses either before, during or after strenuous exercise but preferably at regular intervals on a daily basis over a prolonged period of time as part of a prescribed program to alleviate lameness resulting from navicular disease or as a profoloctic treatment as an attempt to prevent the onset of lameness in horses prone to developing equine navicular disease.

The particular dosage administered in any particular application will vary depending upon the horse being treated, in addition to other factors. In general, however, the amounts of pentoxifylline administered will be within the range of 6 to 30 gm on a daily basis.

The pentoxifylline is preferably administered in admixture with a pharmaceutically acceptable carrier. A variety of pharmaceutically acceptable carriers may be used for purposes of the present invention. In this regard, pentoxifylline may be administered orally, parenterally or intravenously.

For example, in the preparation for parenteral or intravenous injection, a suitable pharmaceutical carrier would be sterile water, saline solution, glucose solution and mixtures thereof. Injectable suspensions could also be formulated in which case appropriate liquid carriers, suspending agents and the like would be employed.

Preferably, however, pentoxifylline is administered orally. Although liquid pharmaceutical carriers including water, glycose, oils and alcohols may be used, it is most preferred to formulate pentoxifylline in a dry or solid preparation, for example in the form of a pill, such as tablets, capsules, caplets and the like. Thus, preferred dosage formulations include pentoxifylline in admixture with sugars, starches, kaolin, lubricants, binders and the like, with sugars, such as confectioners sugar, corn sugar and mixtures of confectioners sugar and corn sugar being most preferred.

The composition preferred for purposes of the present invention includes on a total weight basis preferably about 7% pentoxifylline and about 92% sugar which is preferably at least one member selected from the group consisting of confectioners sugar, corn sugar and mixture of confectioners sugar and corn sugar, and preferably including about 8.5% confectioners sugar and 84% corn sugar, in addition to colloidal silicon dioxide preferably present at a level of about 0.25% as well as artificial colors, preservatives, humectants, antimicrobial agents and the like with about 0.16% artificial color, such as Tartrazine Lake (34% Yellow #5) being preferred.

The most preferred composition for purposes of the present invention on a total weight basis consists essentially of about 7.2% pentoxifylline, about 8.5% confectioners sugar, about 83.895% corn sugar (Cerelose$_{tm}$), about 0.247% colloidal silicon dioxide (Sipernat 22S$_{tm}$) and about 0.158% Tartrazine Lake (34% Yellow #5).

In view of the difficulties in administering medications and pharmaceutical preparations orally to horses, it is preferred to dilute the pentoxifylline with a pharmaceutically acceptable carrier. It is been found to be particularly suitable for purposes of the present invention to formulate pentoxifylline in a powder formulation in the ratio of pentoxifylline to powder within the range of about 1:20 and preferably about 1:13. The preferred powder or particulate material for purposes of the present invention is sugar.

As previously mentioned, it is preferred to administer daily doses of pentoxifylline for a prescribed period of time in order to alleviate lameness caused by navicular disease. In this regard, daily doses of between 6 gm and 30 gm of pentoxifylline administered for a period of between 4–6 weeks have been found to be effective in completely eliminating navicular lameness. It is preferred to administer the daily doses tid. In this regard, powder, tablet or capsule formulations, containing between 2–10 gm of pentoxifylline should be administered for this purpose. As previously indicated, the amount of daily doses is dependent on a variety of factors, including the size of the horse being treated.

TEST

EFFICACY OF ORAL PENTOXIFYLLINE IN THE TREATMENT of NAVICULAR DISEASE IN HORSES

The purpose of the following study was to assess the efficacy of pentoxifylline in the treatment of navicular disease in horses; to establish an appropriate dosage and treatment interval, and to identify adverse effects from treatment.

Twenty-seven horses entered the study between September 1985 and March 1986.

Pentoxifylline was supplied as an oral powder prepared in individual plastic vials of 2 gm Pentoxifylline mixed with 4 gm icing sugar, to ensure palatability.

Diagnosis of navicular disease was made using the following criteria:
1) history - including clinical and previous treatment history.
2) clinical examination
   lameness observed at walk and while lunging to the left and to the right.
   conformation of foot
      contracted heels
      excessive wearing of toe
      flat soles
   hoof tester response (where foot size permitted)
   examination for heat, digital pulse in feet
3) diagnostic posterior digital nerve block
   horses not sound following bilateral desensitization of the posterior digital nerves were not admitted into the study
4) radiographic examination of confirmation of disease as noted by classical navicular lesions, on a minimum of three views
   1 anteroposterior 60°
   2 straight lateral
   3 caudal tangential Follow-up observations occurred weekly during the six week treatment period, and for a final time approximately 4 weeks after the 6 week treatment period was over. The follow-up visits consisted of a lameness evaluation on the lunge line, at the walk and at rest. Owners/trainers were asked to report any side effects observed that may or may not have been related to Pentoxifylline therapy, and any other problems that had arisen during the week, concurrent medications administered for other causes, and the horse's progress while being exercised. Blood samples were drawn prior to first treatment, at 3 weeks, and at 6 weeks for routine hematological and clinical chemistry profiles. Samples were drawn prior to lameness examination after the horse had been resting quietly in the stall. Most samples were drawn early in the afternoon, and were immediately submitted to Metro Animal Laboratories, Bloor Street, Toronto.

TABLE

Results (27 cases included)

Demographic variables

1) Age range = 3-25 (years)
   mean = 10.08 (years)
   *n = 25

| | | | |
|---|---|---|---|
| 2) | Breed | Thoroughbred | 4 |
| | | Standardbred | 1 |
| | | Quarterhorse | 5 |
| | | Irish Hunter | 2 |
| | | Canadian Hunter | 2 |
| | | Appaloosa | 1 |
| | | Pony | 1 |
| | | X-Bred | 6 |
| | | Hanoverian X | 3 |
| | | Percheron X | 1 |
| | | Trachaner X | 1 |
| | | n | 27 |
| 4) | Sex | Male | 0 |
| | | Female | 4 |
| | | Gelding | 23 |
| | | n | 27 |
| 5) | Occupation | Jumper | 10 |
| | | Hunter | 7 |
| | | Roping | 2 |
| | | Dressage | 2 |
| | | Riding School | 2 |
| | | Pacer | 1 |
| | | Police Horse | 1 |
| | | N/A | 2 |
| | | n | 27 |

Clinical Variables

| | | | |
|---|---|---|---|
| 1) | Side Affected | Right | 7 |
| | | Left | 11 |
| | | Bilateral | 9 |
| | | n | 27 |
| 2) | Feet Affected | Right | 16 |
| | | Left | 20 |
| | | n | 36 feet involved in 27 horses |
| 3) | Duration of Lameness | Range | 10 days-14 years |
| | | mean | 2.1 years |
| | | n | 27 |

4) Stage of Disease (Based on Radiographic Pathology)

| | |
|---|---|
| incipient | 11 |
| incipient to intermediate | 2 |
| intermediate | 8 |
| intermediate-advanced | 2 |
| advanced | 4 |
| n | 27 |

*2 horses described only as 'aged' not included

Treatment Regime

Treatment was administered daily for 42 days. The initial dose was 2 gm tid or 6 gm daily as response was not considered consistently optimal at the 2 gm bid treatment regime.

| | | Dosages Administered | |
|---|---|---|---|
| 1) | 2 gm bid | 6 horses | (# 1, 4, 6, 7, 8, 13) |
| 2) | 2 gm tid | 13 horses | (# 12, 16 to 27) |
| 3) | 2 gm bid 3 weeks<br>2 gm tid 3 weeks | 2 horses | (# 2, 15) |
| 4) | 2 gm bid 2 weeks<br>2 gm tid 4 weeks | 3 horses | (# 5, 9, 10) |
| 5) | 2 gm bid 4 weeks<br>2 gm tid 2 weeks | 1 horse | (# 3) |
| 6) | 2 gm bid 1 week<br>2.gm tid 5 weeks | 1 horse | (# 11) |
| 7) | 2 gm tid 2 weeks | 1 horse | (# 14) |

Horse number 14 in category 7 was initiated at 2 gm tid. However, as sweating was being reported by the owner, the dosage was decreased to 2 gm bid after two weeks.

Violations of Protocol

In four horses, a violation of the treatment regime had occurred:

| | |
|---|---|
| #7 Navajo | picky eater - may not have ingested full dosage at each treatment |
| #15 Cheska | trainer forgot to feed her the medicine during week 3 |
| #18 Molson | change of barn personnel led to inconsistent feeding |
| #8 Hemmingway Hanover | raced and refractured $P_3$ at week 4 and was dropped from study. |

Drop Outs

Two horses became drop outs due to injuries sustained during the course of the study.

| | |
|---|---|
| #7 Navajo | developed abscess in his hock and became too lame to evaluate<br>Abscess required treatment<br>Was available for 4 weeks |
| #8 Hemmingway Hanover | fractured $P_3$ during a race and dropped out after 4 weeks |

Diagnosis

All horses were diagnosed as having had navicular disease, except for one horse, Hemmingway Hanover #8, who had a fracture of $P_3$.

Many horses had radiographic findings not related to navicular disease, most of which were assessed as not contributing to the present lameness.

| | Lesion | Horses Involved |
|---|---|---|
| 1) | $P_3$ wing fracture | #6, #8 |
| 2) | $P_3$ rotation | #7 |
| 3) | bowed tendons | #1, #9, #19 |
| 4) | thrush | #9, #11, #17 |
| 5) | ringbone | #1, #17, #18, #23, #24, #25, #26 |
| 6) | splint bone | #2 |
| 7) | sidebone | #5, #13, #21, #25 |
| 8) | soft tissue calcification | #10, #25 |
| 9) | avulsion fractures $P_2$ | #17 |

Navicular bone fractures or chips were present in 4 horses, as follows:

| | | |
|---|---|---|
| #4 | Ensign | Fractured navicular bone (old) |
| #6 | Pas de Quoi | avulsion fracture distal border |

-continued

| #10 | Red | possible transverse fracture |
| #12 | Guppo | avulsion fractural distal border |
| #26 | Impact 76 | avulsion fracture proximal border |

Two horses had other concurrent problems during the course of the study which were regarded as contributing to the animal's lameness, although both continued in the study:

| #25 | Damascus | chronic LH lameness that he would warm up out of |
| #14 | Cash in McCue | superficial abscess front of left front fetlock that drained at week 4. |

Severity of Lameness at Onset of Study

Horses were characterized as either severely lame, moderately lame, or slightly lame, as follows:

| Degree of Lameness | n | Horse Numbers |
|---|---|---|
| Severe | 8 | 2, 7, 8, 9, 11, 15, 16, 18 |
| Moderate | 11 | 1, 3, 4, 10, 12, 14, 19, 20, 23, 25, 27 |
| Slight-Moderate | 6 | 5, 6, 17, 21, 22, 24 |
| Slight | 2 | 13, 26 |
| n = | 27 | |

Clinical Signs Present

There were basically 10 clinical signs or abnormalities noted, as follows:

| Clinical Sign | Number of Horses |
|---|---|
| 1) nods | 16 |
| 2) points | 10 |
| 3) short strided | 9 |
| 4) stumbles | 5 |
| 5) worn toe | 5 |
| 6) flat footed | 5 |
| 7) contracted heels | 5 |
| 8) sheared or uneven heels | 5 |
| 9) heat | 3 |
| 10) digital pulse | 1 |

A list of signs present per horse is provided below.

Previous Treatments

Most of the horses had affected for a long time and had therefore received prior treatment at various times throughout their lameness period.

The treatment history consisted of the following:

| Previous Treatment | Number of Horses |
|---|---|
| Phenylbutazone | 19 |
| Banamine | 3 |
| Isoxsuprine | 4 |
| Arquel | 3 |
| Cryotherapy | 4 |
| Neurectomy | 2 |
| Serapin | 2 |
| Trental | 3 |

Efficacy of Pentoxifylline

Treatment response was classified as excellent, good, fair, or poor.

| Response | Number of Horses (%) |
|---|---|
| excellent | 15 (63) |
| good | 5 (20) |
| fair | 2 (8) |
| poor | 3 (13) |
| | n = 25* |

*7, 8 - drop outs - not evaluated

Response over time is plotted as graph 1, from which it can be seen that maximal response occurred at 4 weeks and did not regress between 4 and 6 weeks. Response was however evident at 1 week and was marked at 2 and 3 weeks. Soundness was subjectively rated by the veterinarian on a percent basis. Percent soundness at the study's onset was subtracted from percent soundness at the study's conclusion, and this difference was plotted as a histogram (graph 2), to show the magnitude of improvement with the 6 week course of treatment. At week 4 there was an average of 57% improvement. For instance, horse number 3 was rated as 25% sound at the onset of the study, and 100% sound after six weeks, yielding an improvement of 75%.

The following compares the severity of lameness at onset and the duration of lameness to treatment response.

| Lameness at Onset | Response | | | | |
|---|---|---|---|---|---|
| | Excellent | Good | Fair | Poor | n/a |
| severe (8) | 2 | 1 | — | 3 | 2 |
| moderate (11) | 7 | 1 | 2 | — | 1 |
| slight-moderate (6) | 6 | — | — | — | — |
| slight (2) | — | 2 | — | — | — |

All poor responses (3) came from severely lame cases. However two horses had an excellent response even though they were severely lame at the onset. Horses with moderate lameness had a preponderance of excellent responses.

| Duration of Lameness | Response | | | | |
|---|---|---|---|---|---|
| | Excellent | Good | Fair | Poor | n/a |
| 6 months (7) | 4 | 1 | — | 1 | 1 |
| <6 months, >2 years (11) | 7 | 2 | 1 | 1 | — |
| 2 years– 5 years (5) | 2 | 1 | — | 1 | 1 |
| 5 years (4) | 2 | 1 | 1 | — | — |

Therefore, poor responses were distributed among acute, subacute and very chronic cases. Similarly excellent responses were noted in 2 out of 4 horses (50%) of cases of greater than 5 years duration, and in 11 out of 18 horses (61%) with duration of lameness of up to two years.

The three 'poor' responses or treatment failures were horses #9 (It's Casual), #15 (Cheska), and #18 (Molson). Horse #9 (It's Casual) never showed significant improvement during the six week treatment course. He had had a bilateral neurectomy 18 months previously, while the left front posterior digital nerves had been reneurectomized 6 months previously. This horse was, therefore, a poor candidate for the study from the outset. Horse #15 (Cheska) showed virtually no response for the first 3 weeks, when it was learned that the drug had not been administered properly in the previous week. The dosage was increased from 2 gm bid to 2 gm tid and at the end of 4 weeks, she was evaluated 90% sounder. However, at weeks 5 and 6 she was as lame as at the beginning. During the 4th week, she was subjected to jumping which precipitated the acute lameness recurrence. At the week 3 visit, the veterinarian elected to block her foot again and he also took radiographs of her left front fetlock joint and pastern, to verify the original diagnosis, which was being questioned due to the apparent lack of response. The original diagnosis of navicular was confirmed and, therefore, this case was assessed as refractory to pentoxifylline treatment. Horse #18 (Molson) had shown marked improvement at week 3 and week 5. However, at week 6 he was as lame as at the onset of the study. Radiographs revealed gross lesions of the right front navicular bone, his sounder leg, but were not remarkable for the left front navicular bone. He was a relatively acute case with intermittent lameness of his front limb over the previous 5 months, that had responded to phenylbutazone treatment. At the initial visit, he was severely lame on his left front, and showed a right front lameness when the posterior digital nerves of the left leg were anesthetized. It was also learned that drug administration had been inconsistent due to a change in barn personnel. Although he was refractory to treatment, it is difficult to know to what extent the irregular treatment regime influenced the results.

Long Term Efficacy

Ten horses received a further follow up evaluation after termination of the 6 week treatment period. The horses are listed below, along with the date of visit (weeks post-initiation of study) and the soundness evaluation.

| Status Follow Up Comments (Greater Than 6 Weeks) | | | | |
|---|---|---|---|---|
| 1 | Jake | Improved | 9 weeks later | 80% sound |
|   |      |          | 11 weeks later | still sound and being ridden |
|   |      |          | 20 weeks later | 100% sound and being ridden |
| 2 | Lucky Lion | Improved | 10 weeks later | 2 gm once per day maintenance |
| 3 | Remeny | Improved | 12 weeks later | hunting sound |
|   |        |          | 18 weeks later | very sound |
| 4 | Ensign | Same | 8 weeks later | sore RF |
|   |        |      | 11 weeks later | sound again when given 2 gm/day |
| 5 | Wessex | Improved | 15 weeks later | sounder than at end of the 6 weeks |
| 11 | Capital Gains | Improved | 8 weeks later | less sound without drug |
| 13 | Peaches 'N Cream | Same | 11 weeks later | as sound as when entered study |
| 14 | Cash in McCue | Improved | 12 weeks later | 100% sound |
| 16 | B. E. Skipper | Improved | 11 weeks later | 90% sounder and riding again; looks 100% sound in field |
| 20 | Innovator | Worse | 7 weeks later | 80% sounder to LT; 90% sounder to RT |
|    |           |       | 9 weeks later | lame LF as before treatment |

Seven of these 10 horses were considered sounder than they had been at the end of the 6 week treatment period. Three horses (Innovator, Capital Gains, and Ensign) were judged to be sore again 2 weeks after cessation of treatment. Ensign was put on a maintenance dose of 2 gm daily of pentoxifylline after the 8 week visit and was sound when seen at 11 weeks. Innovator was as lame at 9 weeks as he had been prior to treatment, indicating a significant regression within the 3 week period of treatment withdrawn.

Therefore the following patterns were noted when drug administration ceased. In some cases, horses maintained the improvement noted at 6 weeks and other horses regressed rapidly when treatment ended.

Side Effects

Four horses experienced unusual occurrences throughout the course of the study that were reported by the owners or observed by the veterinarian. Only 1 instance was judged to be a drug-related side effect by the veterinarian.

| Effect | Number | Horses |
|---|---|---|
| Sweating | 2 | 14, Cash in McCue - 5 episodes of sweating after 2 weeks - drug-related |
|          |   | 20, Innovator - occasional sweating - unrelated |
| Colic | 1 | 23, Greek Anthem, between weeks 2 and 3; previous history of colic |

The sweating episodes that occurred in horse #14 (Cash in McCue) were judged to be drug-related. Sweating has also been reported as an occasional human side effect. The sweating reported in horse #20 (Innovator) was assessed as not a genuine drug-related side effect by the veterinarian.

Laboratory Results

Clinical chemistry results revealed that all values were within the reference range for the equine species, with the exception of potassium, for which five horses had values slightly below the laboratory normal limit prior to treatment. Mean values did not differ significantly (based on the t-test) at the 3 week or 6 week sampling times, compared to baseline values, except for calcium where the mean decreased from 11.57 at the baseline to 11.33 at week 3, p 0.01. However, no clinical importance is attached to this finding as all values were within reference range. Therefore, all blood chemistry values indicated no clinical effect from pentoxifylline treatment. Hematology values were also within normal limits throughout the study. Platelets showed a consistent increase between baseline and week 3 and baseline and week 6. The mean platelet count at baseline was 172,926 (n=27). This mean increased to 204,222 (n=27) at week 3, representing an average increase of 31,296, which was a statistically significant change (p 0.01). Twenty-five horses exhibited an increase in platelet count during this interval, indicating a drug-related effect. The mean platelet count at week 6 was 209,360 (n=25) representing an increase of 36,120 from baseline (p 0.01), and a smaller magnitude increase of 4,520 between weeks 3 and 6. However, in spite of the increase in actual platelet count, 13 horses had a lower platelet count at week 6 than at week 3. Thus the bulk of the change occurred between baseline and week 3, and appears to have stabilized at that level.

Conclusion

The results of the previously discussed preliminary investigation in 27 horses substantiate the efficacy of pentoxifylline in the treatment of navicular disease.

The study was performed by a licensed veterinarian. The dosage selected was extrapolated from the human dosage on a mg/kg basis.

There was a normal distribution of age, sex, breed and occupation. Duration of lameness ranged between 10 days and 14 years, with a mean of 1.9 years. Lameness was mild to severe and radiographic lesions supported the diagnosis in every case.

During the 4 to 6 week treatment regime, horses were evaluated weekly. Treatment response was assessed by the return to soundness and useful work. Treatment was considered excellent in 63% of the cases, good in 17% and fair in 8%.

These results are evidence that the a suitable dosage form of pentoxifylline for the treatment of equine navicular disease is effective.

| Test | Table of Means for All Horses Blood Chemistry | | | | |
|---|---|---|---|---|---|
| | Baseline Mean n = 27 | 3 Weeks Mean n = 27 | 6 Weeks Mean n = 25 | Normal Values | |
| Na | 137.2 | 137.1 | 138.2 | 139–145 | mmol/L |
| K | 3.67 | 3.41 | 3.74 | 2.7–4.5 | mmol/L |
| Cl | 98.8 | 98.9 | 98.9 | 97–106 | mmol/L |
| Ca | 11.57 | 11.33 | 11.34 | 10.6–12.2 | mmol/L |
| Mg | 2.03 | 2.09 | 2.08 | 2.0–3.0 | mmol/L |
| Phos | 2.81 | 2.84 | 2.65 | 2.4–4.0 | mmol/L |
| BUN | 16.46 | 16.71 | 15.67 | 8–18 | mmol/L |
| TSP | 6.14 | 6.09 | 6.11 | 5.8–7.7 | g/L |
| SGOT | 211.1 | 211.3 | 212.8 | 160–300 | U/L |
| SGPT | 5.3 | 5.2 | 5.0 | 5–15 | sigma |
| Alk Phos | 5.93 | 5.87 | 5.79 | 3–12 | U/L |
| TBR | 1.70 | 1.66 | 1.84 | 0.4–4 | umol/L |

| Test | Table of Means for All Horses Hematology | | | |
|---|---|---|---|---|
| | Baseline Mean n = 27 | 3 Weeks Mean n = 27 | 6 Weeks Mean n = 25 | Normal Values |
| WBC | 8,678 | 8,311 | 8,564 | 7,00–9,500 |
| RBC | 8,896,296 | 9,027,778 | 9,092,000 | 8.2–11.0 × $10^{12}$/L |

| Test | Table of Means for All Horses Hematology (continued) | | | |
|---|---|---|---|---|
| | Baseline Mean n = 27 | 3 Weeks Mean n = 27 | 6 Weeks Mean n = 25 | Normal Values |
| Hb | 92.1 | 93.1 | 94.0 | 85–108 gm % |
| HCT | 39.7 | 39.9 | 40.6 | 37–48 |
| Polycytes | 56.9 | 54.3 | 57.2 | 35–68% |
| Band | 0.3 | 0.0 | 0.2 | 0.0–0.2% |
| Lymph | 38.6 | 40.7 | 37.6 | 26–57% |
| Eos | 2.1 | 2.3 | 1.8 | 0–10% |
| Mono | 1.9 | 2.2 | 2.7 | 0–6% |
| Baso | 0.4 | 0.5 | 0.5 | 0–1% |
| Plat | 172,926 | 204,222 | 209,360 | 80–397 × $10^9$/L |
| ESR | 18.4 | 21.0 | 21.1 | 0–38 mm in 20 min |

TABLE

| PLATELETS | Baseline n = 27 | Week 3 n = 27 | Week 6 n = 25 |
|---|---|---|---|
| Mean | 172,926 | 204,222 | 209,360 |
| SD | 14,657 | 27,956 | 33,924 |
| Minimum | 148,000 | 160,000 | 161,000 |
| Maximum | 208,000 | 260,000 | 283,000 |
| Average Increase | | 31,296 | 36,120 |
| Minimum Increase | | 8,000 | 4,000 |
| Maximum Increase | | 95,000 | 91,000 |
| Number of horses increased since baseline | | 25 | 20 |

Therefore, pentoxifylline has been found to be effective in alleviating the lameness of navicular disease of varying severity and duration. A lag period between initiation of treatment and maximum response obtained is similar to the two week period reported in man. A 6 gram dosage divided tid appears to have achieved the best results and harmful side effects have not been identified.

It is further understood that although the invention has been specifically described with reference to particular means and embodiments, the foregoing description is that of preferred embodiments of the invention. The invention, however, is not limited to the particulars disclosed but extends to all equivalents, and various changes and modifications may be made in the invention without departing from the spirit and scope thereof.

What is claimed is:

1. A method of treating a horse suffering from navicular disease comprising:
   administering to said horse an amount of a composition comprising pentoxifylline, in a daily dose of between about 6 gm–30 gm, to alleviate lameness resulting from navicular disease.

2. The method of treating a horse suffering from navicular disease in accordance with claim 1, wherein said daily dose is about 6 gm.

3. The method of treating a horse suffering from navicular disease in accordance with claim 1, wherein said daily dose is administered tid.

4. The method of treating a horse suffering from navicular disease in accordance with claim 1, wherein said daily dose is administered for between 4–6 weeks.

5. The method of treating a horse suffering from navicular disease in accordance with claim 1, wherein said composition comprises a mixture of said pentoxifylline and sugar.

6. The method of treating a horse suffering from navicular disease in accordance with claim 5, wherein said pentoxifylline and said sugar are present in said composition in a ratio within the range of about 1:1 to 1:20.

7. The method of treating a horse suffering from navicular disease in accordance with claim 8, wherein said ratio is about 1:13.

8. The method of treating a horse suffering from navicular disease in accordance with claim 7, wherein said composition is administered 2 gm tid.

9. The method of treating a horse suffering from navicular disease in accordance with claim 8, wherein said amount is administered tid.

10. The method of treating a horse suffering from navicular disease in accordance with claim 9, wherein said administering is performed daily for between 4-6 weeks.

11. The method of treating a horse suffering from navicular disease in accordance with claim 7, wherein said composition comprises about 7% pentoxifylline by total weight.

12. The method of treating a horse suffering from navicular disease in accordance with claim 11, wherein said composition comprises about 92% sugar by total weight.

13. The method of treating a horse suffering from navicular disease in accordance with claim 12, wherein said sugar comprises about 84% corn sugar and about 8.5% confectioners sugar by total weight of said composition.

14. The method of treating a horse suffering from navicular disease in accordance with claim 13, wherein said composition on a total weight basis comprises about 0.25% colloidal silicon dioxide.

15. The method of treating a horse suffering from navicular disease in accordance with claim 14, wherein said composition on a total weight basis comprises about 0.16% artificial color.

16. The method of treating a horse suffering from navicular disease in accordance with claim 15, wherein said composition of a total weight basis consists essentially of 7.2% pentoxifylline, 8.5% confectioners sugar, 83.895% corn sugar, 0.247% colloidal silicon dioxide, and 0.158% artificial color.

* * * * *

UNITED STATES PATENT AND TRADEMARK OFFICE
CERTIFICATE OF CORRECTION

PATENT NO. : 5,077,296

DATED : December 31, 1991

INVENTOR(S) : Alan DRIZEN

It is certified that error appears in the above-identified patent and that said Letters Patent is hereby corrected as shown below:

Column 15, line 8, change "8" to --6--.

Column 16, line 20, change "of" to --on--.

Signed and Sealed this

Fourth Day of May, 1993

Attest:

MICHAEL K. KIRK

Attesting Officer

Acting Commissioner of Patents and Trademarks